(12) United States Patent
Walthert

(10) Patent No.: US 8,204,710 B2
(45) Date of Patent: Jun. 19, 2012

(54) DYNAMIC POSTURAL APPARATUS FOR DETECTING A BALANCED BIPED POSTURE

(76) Inventor: Nicole Walthert, Orleans (FR)

(*) Notice: Subject to any disclaimer, the term of this patent is extended or adjusted under 35 U.S.C. 154(b) by 465 days.

(21) Appl. No.: 12/441,766

(22) PCT Filed: Sep. 13, 2007

(86) PCT No.: PCT/FR2007/001490
§ 371 (c)(1),
(2), (4) Date: Aug. 19, 2009

(87) PCT Pub. No.: WO2008/034965
PCT Pub. Date: Mar. 27, 2008

(65) Prior Publication Data
US 2010/0023293 A1 Jan. 28, 2010

(30) Foreign Application Priority Data
Sep. 22, 2006 (FR) ...................................... 06 08323

(51) Int. Cl.
*G06F 19/00* (2011.01)
(52) U.S. Cl. ...................................................... 702/101
(58) Field of Classification Search .................. 702/101, 702/173; 177/136, 139; 73/1.08, 1.13
See application file for complete search history.

(56) References Cited

U.S. PATENT DOCUMENTS

| 4,805,637 A | * | 2/1989 | Walthert | 600/587 |
| 4,917,197 A | * | 4/1990 | Waite, Jr. | 177/137 |
| 5,993,400 A | * | 11/1999 | Rincoe et al. | 600/595 |

FOREIGN PATENT DOCUMENTS

| EP | 0519836 | 12/1992 |
| FR | 2619702 | 3/1989 |
| FR | 2639111 | 5/1990 |
| FR | 2648559 | 12/1990 |
| FR | 2725022 | 3/1996 |
| WO | 8701923 | 4/1987 |

* cited by examiner

*Primary Examiner* — Bryan Bui
(74) *Attorney, Agent, or Firm* — Lowe Hauptman Ham & Berner, LLP

(57) ABSTRACT

Scales for detecting equilibrium anomalies of a human body include force sensors under a dynamic. A processing unit determines, from signals of the sensors, the total weight of a subject on the plate. The weight is viewed on a display. Deformable members associated with each sensor provide support along an upward direction of the plate relative to a fixed portion of the scales. A module compares data of the sensors received by the processing unit, to detect a poor distribution of the forces. The display is modified when a poor force distribution is measured by the detector module. The subject can thus exercise dynamically to find a balanced position of his/her feet on the plate.

17 Claims, 3 Drawing Sheets

DYNAMIC POSTURAL APPARATUS FOR DETECTING A BALANCED BIPED POSTURE

RELATED APPLICATIONS

The present application is based on, and claims priority from, FR Application Number 0608323, filed Sep. 22, 2006, and PCT Application Number PCT/FR07/001490, filed Sep. 13, 2007, the disclosures of which are hereby incorporated by reference herein in their entireties.

FIELD OF THE INVENTION

The present invention relates to the field of private apparatuses indicating weight information and/or weight distribution, in particular in the field of weighing a person in a dynamic vertical posture. The invention, by using the principle of distribution of the weight of the body on plantar supports, in the balanced biped position, more particularly relates to an apparatus and a method allowing the display of the weight of the body in equilibrium on a plane and horizontal surface (regardless of the vertical posture (standing-up, half-crouching or crouching)).

BACKGROUND ART

It is known that, under such conditions, the weight of the body is distributed on all the supporting points of both arches of the foot. Each foot has three supporting points, two at the front (heads of the first and fifth metatarsian) and one at the rear (posterior tuberosities of the calcaneum). In the biped equilibrium position on a plane and horizontal ground, the weight of the body is applied by half on each keystone of the arch of the foot, center of the instep, located plumb with the extension of the front edge of the leg, before then being distributed by half on the anterior supporting points and the posterior supporting point of the arch of the foot. In such a vertical upright position, the centre of gravity of the human body (third lumbar vertebra) and the line of gravity are properly placed, the base of support (contour of the feet and space between the feet) is determined, the lower limbs are in the extension of the trunk and the curvatures of the vertebral column attain their characteristic shape. Under these circumstances of biped equilibrium, the weight of the body is distributed in four quarters on the plantar supporting points. Each forefoot and hind foot receives the quarter of the total weight of the body.

In a known way, a comfortable and static standing equilibrium on the plantar supporting points is made possible by the architecture of the human body, the skeleton, the tendons, the soft parts. Under these conditions, the muscular activity of the trunk and of the lower limbs is low. The obtained equilibrium is passive, transient and unstable.

It is known that as soon as there is a loss of equilibrium, i.e. a risk of falling and regardless of the direction, compensating reflex muscular contractions, postural tonus, reestablish equilibrium. Once equilibrium is reached, the activity of anti-gravitary muscles then ceases until the next loss of equilibrium. The muscular activity of the trunk and of the lower limbs is low. The obtained equilibrium is passive, transient and unstable.

Moreover, it is well established that in all the biped vertical crouching positions, flexed lower limbs, unlocked joints, equilibrium is maintained by means of the powerful action of anti-gravitary muscles of the lower limbs and of the column. Under these conditions, the centre of gravity is lowered, equilibrium is more stable, the line of gravity passes through the centre of each instep, the arch of the foot collapses, the length of the feet increases. The supporting points slightly slide, those of the front towards the front of the foot, those of the rear towards the rear of the foot, and the distribution of the weight of the body on the supporting points is the same as in the vertical standing position. The lower the crouching positions, the more the equilibrium is stable and the higher is the tonus of anti-gravitary muscles. In the full crouching position, the centre of gravity is at its lowest point, the equilibrium is very stable, the body folded over itself assumes a fetal form, knees forwards, buttocks rearwards, head forwards, column bent forwards over the whole of its length (the different lines of column curvature vanish), and the activity of the anti-gravitary muscles ceases. The distribution of the weight of the body on the plantar supporting points remains unchanged. This position is a relaxation posture of the body adopted by children and many adults in certain countries.

It is the central nervous system which provides and regulates muscular postural tonus, from propioceptive sensorial information (muscles, tendons, joints), from vestibular (labyrinths) and exteroceptive visual, auditive and tactile information which it receives. In order to reach the state of equilibrium, the application of a complex system with several inputs (sensorial stimulations) and several outputs (muscular reactions) is required. Any change in stimulation (input) causes a dynamic re-equilibration reaction (output). The result is a harmonious and effective posture.

It is known that any movement starts from equilibrium and reaches it. It is also known that the three exteroceptive sensitivities (sight, hearing, plantar touch) in relation with the outside world, act on the postural tonus by adjusting our attitudes and that the sensitivity of the plantar tactile receptors play a major role here. Submitted to the pressure of the weight of the body and to its variations on the one hand, in contact with the ground, to its texture, its irregularities, its level differences on the other hand, the receptors of the plantar tactile corpuscles, by the amount of information which they detect and transmit to the nervous system, are the starters of reflexes ensuring equilibrium.

The plantar touch organ is a sensorial organ, the acuity of which is essentially sustained by walking and crouching. Walking, a symmetrical natural locomotion, provides the advantage, during the phase of foot progression on the ground, of stimulating in turn the tactile perception of each plantar supporting point. Biped crouching strongly activates perception of all the plantar supports during the changes in flattening of the arches of the feet. Since about fifty years, our way of life has changed, which has caused a reduction in the daily walking time below a threshold which is absolutely required for sustaining the perception of the tactile sensitivity of our plantar supports and the ensuing vertical postural reflexes. The increasingly sedentary (sitting) human being of modern societies gradually loses, without being aware of this, perception of his/her plantar supports concurrently with the loss of his/her vertical postural tonus and of the habit of walking in a natural way.

Abnormal and frequent wear of shoe soles (for example only at the heel) is a sign of deficient supports during ambulation: little or no pressure on certain supports and too much pressure on other ones. Accordingly, the equilibrium reflexes are perturbed. Some of these reflexes are not so well activated and lose dynamic efficiency. The tonus of certain anti-gravitary muscles (lower limbs and column) decreases. By losing tonus in the lower limbs (mainly in thighs) crouching becomes painful. Numerous are those which give up. By lack of sustaining sensitivity of plantar supports (notably by walking and crouching), perception of the sensitivity, postural dynamism, coordination of gestures (any gesture starts from one or more plantar supporting points), suppleness and harmony of the shape of the body gradually disappear, obesity symptoms appear at the same time. Confronted with this established fact, it is recommended by all physicians to monitor one's weight and to move, walk or practice a sports activity.

A subject matter of the invention, by reactivating perception of the tactile sensitivity of all of one's plantar supports, dynamic starters of the vertical posture, is to give the possibility to the human having become sedentary, of not only moving, walking, crouching or practicing a sport safely, but also to give him/her back the desire to do this, and of thereby sparing him/her the risks of obesity.

A subject matter of the invention is to give a user the possibility of focusing on the distribution of the weight of his/her body on his/her plantar supports in a situation of verticality (supported on a plane, mobile surface), by having him/her become aware of his/her disequilibrium.

In the prior art, systems with two mobile plates are known with which the distribution of the user's weight on each of his/her legs may be viewed.

Document WO 87/01923 of the same inventor, discloses an apparatus with a single movable plate mounted on springs and provided with an indicator of horizontality of this movable plate. With this apparatus, the user is able to actively correct the weight-bearing supports of both of his/her feet in order to reach equilibrium, which may be viewed by means of the horizontality indicator of the plate. A bubble level allows accurate indication of when equilibrium is attained.

It is possible to insert scales in a recess of the apparatus described in document WO 87/01923. With the resulting assembly, it is then possible to constantly indicate the weight while the user may continue to improve his/her weight-bearing supports on the mobile plate. A drawback of this known apparatus is that the indication of equilibrium is not interactive and insufficiently arouses the desire of the user to adopt good postures for which equilibrium is reached.

In quite another field, the use of slabs with a resistance which depends on force, so-called FSR (Force Sensitive Resistance) slabs, is known, provided with one or two analog outputs at 3 points in order to be connected to a processing-conversion module which is used for interpreting movements of the human body. The slabs with two analog outputs are sensitive to the posture of the individual on the slab, and more specifically to the distribution of his/her weight in space. They are totally independent of the actual weight, so that they may exactly react in the same way with a child or with a 90 kilogram person. These slabs are, for example, used for forming a sensitive ground with the purpose of modulating sounds and lights, for example.

However, these FSR slabs are neither used nor usable for establishing equilibrium diagnoses.

Document FR 2619702 discloses a plate which is made movable, relatively to a system placed on the ground, by means of a single ball-joint link. The information or response provided by the apparatus is static and is especially perceived visually. A global movement of rotation is alone generated by the ball-joint link in order to oppose the equilibrium of the patient, which strongly limits the stimulation of the tactile perception of the plantar supports.

The objective of the present invention is therefore to overcome one or more of the drawbacks of the prior art by defining an apparatus provided with additional indicator functions which may be activated depending on whether equilibrium is reached or not, the apparatus remaining of simple design and with which the equilibrium in the distribution of the weight on the plantar supports may be specifically accounted for.

SUMMARY OF THE INVENTION

For this purpose, an aspect of the invention relates to an apparatus for detecting and correcting equilibrium anomalies of the human body, including a supporting plate, on which a user may take up position, and at least one reference system part which may be positioned on a substantially plane surface, the plate being superposed relatively to the reference system part, characterized in that said plate is supported by at least three elastic deformable units each acting along a direction orthogonal relatively to a plane defined by said reference system part, the deformable units being symmetrically distributed (for example, at least according to a triangle) with respect to a central axis of symmetry of the plate, the apparatus comprising:

a processing unit provided with a processing circuit;
a force sensor placed under each of the deformable members, each sensor delivering a signal sent to the processing circuit, the processing circuit detecting equilibrium between the signals representing the forces and corresponding to a position of perfect equilibrium relatively to the centre of symmetry of the plate, or detecting disequilibrium between these signals; and
means for generating the display of a piece of information in the case of equilibrium and a visual and/or sound indication, modified when a poor distribution of the forces is detected by the processing circuit, the visual and/or sound indication providing indication of equilibrium anomalies to a user.

Thus, according to an aspect of the invention, it is possible to obtain a display of a piece of information such as weight by using sensors which are more or less actuated depending on the distribution of the forces exerted on the plate by the weight-bearing supports of the feet, which advantageously gives the possibility of detecting via the processing circuit whether equilibrium has been reached by the person or not. This equilibrium is reached dynamically because of the presence of the deformable members such as springs which are constantly actuated. The subject has to show concentration and may, by applying pressure on his/her supports, correct his/her disequilibrium, so that his/her perception of all the plantar supports is reactivated in an easy, playful and efficient way.

According to another particularity, the piece of information displayed in the case of equilibrium is the weight of the user, the apparatus thereby defining scales. Except for persons affected by neuromuscular disorders, this apparatus allows anybody to correct his/her posture while monitoring his/her weight, in other words to ensure that his/her fitness is maintained while keeping a check on his/her figure.

According to another particularity, the apparatus includes a casing provided with ground supporting means, the plate being connected to the casing, the force sensors being provided between said supporting means and the plate in order to each provide an electric signal representative of a force detected by the sensor, at least one processing unit for determining from the signals of the sensors, the total weight of a user (of the scales) placed on the plate, the sensors being identical and distributed in areas symmetrical to each other relatively to a central axis of symmetry passing through the centre of symmetry of the plate, characterized in that it comprises:

deformable members associated with each of the sensor areas in order to support along an upward direction the plate and said sensors relatively to the casing;

a module for detecting disequilibrium, including said processing circuit in order to detect by comparison, from sensor data received by the processing unit, a poor distribution of the forces detected by each sensor; and an interface for controlling the display means with which the display may be changed when a poor distribution of the forces is detected by the detection module.

Thus, the user is advantageously allowed to dynamically improve the equilibrium of his/her supports on the plate borne by the deformable members and particular information may be obtained on the display means when equilibrium is reached.

According to another particularity, the apparatus according to the invention comprises means for adjusting the horizontality of the casing.

Thus, the apparatus (which may form scales) may operate on a ground having a lack of horizontality.

According to another particularity, the ground supporting means comprise four legs positioned on the casing, the legs being firmly attached to a fixed base forming the reference system element.

According to another particularity, said control interface allows display of the total weight of the user of the scales depending on the delivery by the detection module of a piece of information representative of detection of equilibrium.

Thus, it is advantageously possible to obtain information on weight by means of the display means, only provided that equilibrium has been reached, the forces received in different areas of sensors then being equal.

According to another particularity, the scales according to the invention comprise four elastic deformable members each vertically aligned with one of the legs.

According to another particularity, the force sensors are distributed under four corners of the plate, and at least one vertical member connected to the reference system element is positioned in the casing in order to avoid displacement of the plate supported by means of deformable members.

According to another particularity, the module for detecting disequilibrium has a predetermined detection threshold so that a difference between the smallest and the largest of the measured forces which remains smaller than the threshold does not allow disequilibrium to be detected.

According to another particularity, the apparatus according to the invention comprises means for selecting among two operating modes:

a conventional mode for displaying the total weight of the user of the scales, regardless of the distribution of the forces detected by each of the sensors; and a dynamic mode for displaying the total weight of the user of the scales, wherein said control interface prevents the display of said total weight as long as a poor distribution of the forces is detected by the detection module.

According to another particularity, the force sensors are preferably sensors with variable electric resistance.

According to another particularity, a bubble level is preferably integral with the casing in order to indicate the horizontality of the casing.

According to another particularity, the plate preferably bears elements for marking the location of both feet, the marking elements comprising at least a middle line relatively to two of the force sensors.

According to another particularity, the scales preferably comprise a short distance communications interface for transmitting data to a display device freely movable relatively to the remainder of the apparatus.

Another object of the invention is to provide a method for adding in conventional scales, a function for detecting equilibrium anomalies of the human body.

For this purpose, an aspect of the invention relates to a method for integrating into scales with a plate and a visual and/or sound indication of weight, a function for detecting equilibrium anomalies of the human body, characterized in that it comprises:

a step for symmetrically distributing force sensors relatively to a central axis of symmetry of the plate of the scales;

a step for associating with each of the force sensors, a deformable member in order to support along an upward direction a portion of the plate and the associated sensor;

a step for connecting to the sensors a comparison module for detecting the distribution of the forces; and a step for integrating an interface (12) for controlling the weight indicating means in order to generate a modified visual and/or sound indication when poor distribution of the forces is detected by the detection module (11), the modification allowing equilibrium anomalies to be indicated to the user.

The invention with its characteristics and advantages will become more clearly apparent from reading the description made with reference to the appended drawings given as non-limiting examples.

DETAILED DESCRIPTION OF THE DRAWING

Figure 1:
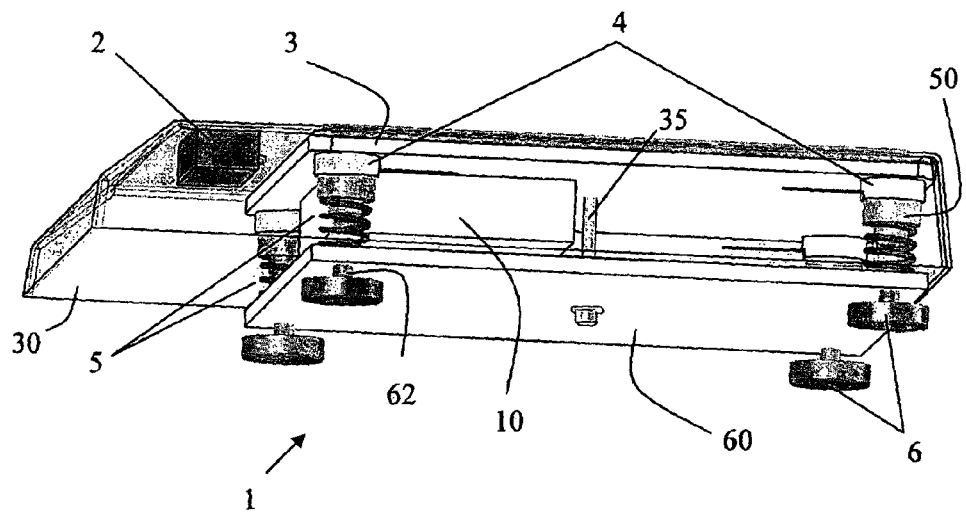
FIG. 1 is a perspective view and transparent view of an embodiment of scales according to a preferred embodiment of the invention.
Figure 2:
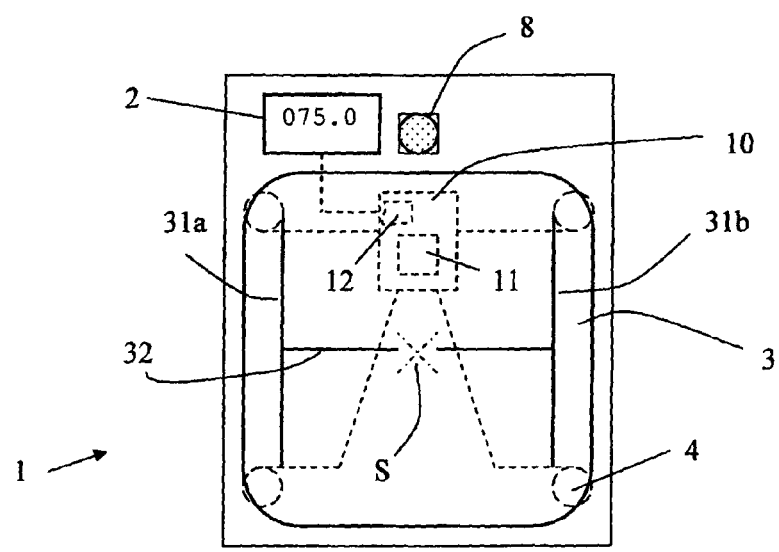
FIG. 2 is a top view of an embodiment of scales according to the preferred embodiment of the invention.

The apparatus may form scales (1) as illustrated in FIGS. 1 and 2. It comprises a casing (30) provided with ground supporting means (6) such as legs, a mobile plate (3) connected to the casing (30), force sensors (4) provided between said bearing means (6) and the plate (3) in order to each provide an electric signal representative of a force detected by the sensor (4). This signal may be a voltage. The ground supporting means for example comprise four legs positioned under the casing (30), the legs being firmly attached to a fixed base (60). The rigid plate (3) is positioned under the upper portion of the casing (30) and rests on the fixed base (60) via deformable members (5) such as springs or equivalent elastic components. The springs are selected in order to withstand large weights. Thus, a set of four force springs may withstand a much larger load than 100 kilograms, for example. The plate (3) is used as a support for the feet of the user. In the example of FIG. 1, the casing (30) comprises an upper window in order to show the display of the weight (2) and the level (8).

In a preferred embodiment of the invention, the sensors (4) are identical and distributed in areas symmetrical to each other relatively to a central axis of symmetry (S), as notably illustrated in FIG. 2. This central axis (S) of the plate (3) is vertical when the scales are placed on horizontal ground. Means (8, 62) for adjusting the horizontality of the casing (30) are provided in the case of lack of horizontality of the grounds, so as to make the central axis of symmetry (S) vertical. One or several legs may be provided with a thumb-wheel system (62) or an equivalent system (with a ball-joint, etc.) in order to adjust the horizontality of the casing (30). The bubble level (8) integral with the casing (30) provides indication of the horizontality of the casing (30). In one alternative, the bubble level (8) may be replaced with a pendulum associated with sensors detecting the displacements of the pendulum in order to provide an indication of horizontality.

The scales (1) are provided with at least one processing unit (10) in order to determine from the signals of the sensors (4) the total weight of a user of the scales placed on the plate (3). This total weight may, for example, be inferred from the sum of the output signals of the sensor (4), after analog/digital conversion. Display means (2) of a type known per se are provided in order to indicate the determined total weight. The deformable members (5) are associated with each of the sensor areas (4) in order to support along an upward direction the plate (3) and said sensors (4) connected to the casing (30). Poor distribution of the forces depending on the areas may advantageously be detected by a processing circuit forming a module (11) for detecting disequilibrium. This module (11) uses the data from the sensors (4), received by the processing unit (10) for detecting by comparison a poor distribution of the forces received on the different sensor areas (4).

The deformable members (5) each exert a reaction force exactly corresponding to the received proportion of weight. Thus, they allow the user as soon as he/she is placed on the plate (3), to feel the reaction differences at his/her plantar supports, without there being any stimulations other than those caused by his/her own weight. Unlike a conventional weighing apparatus which only gives the weight of a user in a passive situation, the apparatus according to the invention allows the weight to be given in a dynamic verticality. Indeed, with this apparatus, it is possible to awaken weight-bearing sensations of the user, to bring the efficient verticality reflexes into play and to develop the tonus of all the anti-gravity muscles (lower limbs and trunk).

When a poor distribution of the forces is detected by the module (11), the latter provides information to the interface (12) for controlling the display means (2). In this case, the weight display is blank. As an example, when the control interface (12) receives equilibrium information stemming from the detection module (11), the interface immediately allows display of the total weight of the user of the scales. When the differences between the measured forces are detected by the module (11) for detecting disequilibrium, then the display may remain blank or display a piece of default information other than the measured weight. The detection module (11) and the control interface (12) may be implemented in the processing means of the processing unit (10).

In an embodiment of the invention, the casing (30) is provided at its four corners, at right angles to the legs, with four elements used as guides for the deformable members (5) formed by the springs. The four deformable spring members (5) are therefore each aligned vertically with one of the legs. The springs, advantageously in steel or in any other material with comparable strength, are of equal height and tare and with sufficient resistance to crushing in order to avoid the possibility of the plate (3) abutting against the base (60) when it supports its load. The plate (3) is of a similar size to that of the base (60) in the example of FIG. 1 and rests through its four corners on protrusions (50) with inverted shoulders. The upper portion of the springs bears upon the inverted shoulders of these protrusions (50).

The force sensors (4) are distributed under four corners of the plate (3). In the example of FIG. 1, a vertical member (35) connected to the fixed base (60) is positioned in the casing (30) in order to avoid vertical displacement of the plate (3). This vertical member (35) may consist in a rod crossing the plate through a hole made in the latter. The hole is central and sufficiently large relatively to the dimensions of the section of the rod so that the mobile plate (3) may have a sufficient degree of freedom during all its changes in inclination. Beyond a threshold of about 5°, the plate will abut on the vertical member at the central hole.

Figure 4:
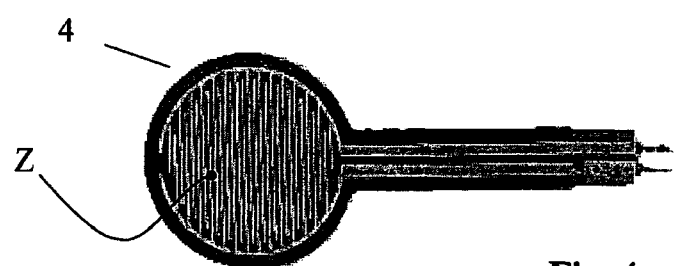
FIG. 4 is an illustration of an exemplary force sensor used in scales according to a preferred embodiment of the invention.

With reference to FIG. 1, the sensors (4) may be inserted between the protrusions (50) or similar abutment elements and the plate (3). The sensors (4) are, for example, force detection resistances FSR (Force Sensitive Resistance). Their structure is extremely simple, as illustrated in FIG. 4: these are two sheets of polymer(s) laminated together (their thickness not exceeding 0.75 mm). Each sensor (4) of the FSR type responds to a force by decreasing its electrical (ohmic) resistance all the more when one presses more strongly on the transducer component (Z). One of the polymer sheets is covered with a network of electrodes and the other sheet is covered with a semiconducting material. Not very sensitive to noise and vibrations, its wide impedance range allows the use of a simplified electronic interface. In a way known per se, the mechanical interface of the force sensors (4) used provides a sufficiently "firm" and resistant support. As a non-limiting example, FSR force sensors marketed by Interlink Electronics® may be used for expressing as electric signals the forces received in the different portions of the plate (3). Other types of equivalent force sensors may naturally be used.

Figure 3A:
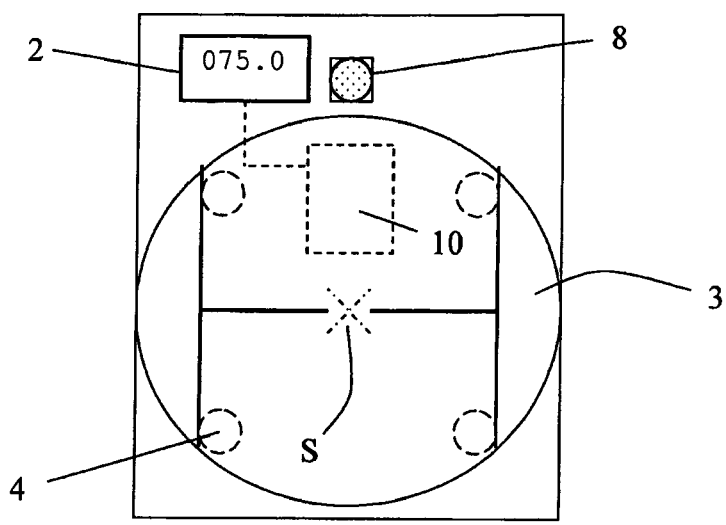
FIGS. 3A and 3B are drawings of exemplary embodiments having different supporting plates.
Figure 3B:
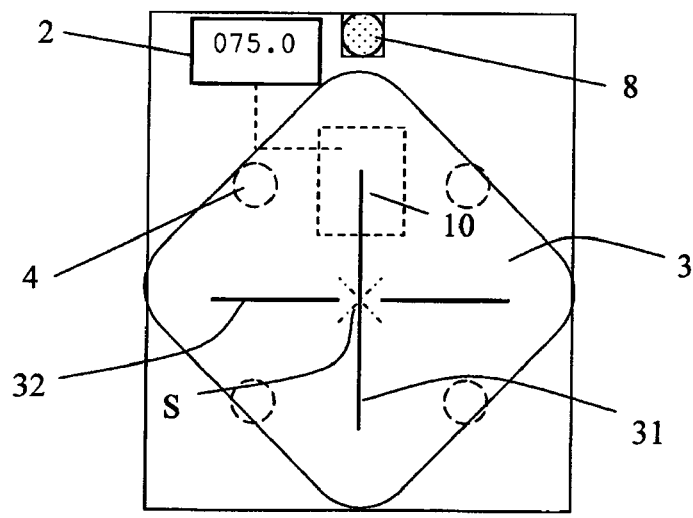

With reference to FIGS. 2, 3A and 3B, it is understood that the distribution of the forces is carried out in four areas distributed around the axis of symmetry (S) of the plate (3) and this, regardless of the contemplated shape for the plate (3). The plate (3) may quite be both globally rectangular or square as in FIGS. 2 and 3B, or ovoid/circular as in FIG. 3A. The sensors have merely to be well distributed in each of the four areas associated with the areas of the plantar supports, respectively.

In an embodiment of FIGS. 2, 3A and 3B, the plate (3) bears elements for marking the location of both feet. For example, the marking elements comprise at least one transverse middle line (32) relatively to two of the force sensors (4). This middle line (32) tells the user that he/she should place each of his/her feet straddling this middle line, so that each instep (portion of the foot corresponding to the keystone of the arch of the foot) is plumb with this middle line (32). Other sagittal lines (31a, 31b) are materialized on the plate (3). They indicate the location of the external edge of each foot (fifth metatarsian) and allow each foot to be placed in the position which ought to be adopted. In the alternative of FIG. 3B, the plate (3) includes an axial line (31) separating the area dedicated to the right foot from the area dedicated to the left foot. A middle line (32) may be drawn orthogonally to this axial line (31) in order to separate the area dedicated to the forefeet from the area dedicated to the hind feet.

Figure 6:
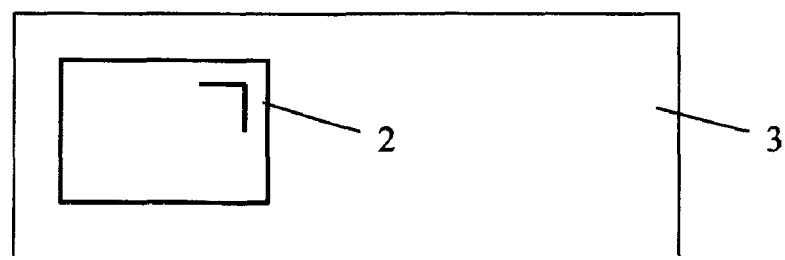
FIG. 6 is an illustration of an exemplary display while a subject was using the apparatus of FIG. 1.

The apparatus may relatively to a positioning grid on the plate (3) provide an indication of the origin of the disequilibrium: a disequilibrium towards the front, towards the rear, towards one side, both on one side and towards the front or towards the rear. With reference to FIG. 6, this indication is given by luminous lines which belong to an interface for displaying numerical of alphanumerical characters. The weight may be displayed by this interface only in the case of equilibrium. The combined display of one line from the top and one line from the right is achieved when the distribution of the measured forces is unbalanced both towards the front and towards the right. The display unit (2) is placed on the front portion of the apparatus, for example, at the plate (3) or may be raised and either connected by wire or not to the processing circuit of the apparatus.

Figure 5:
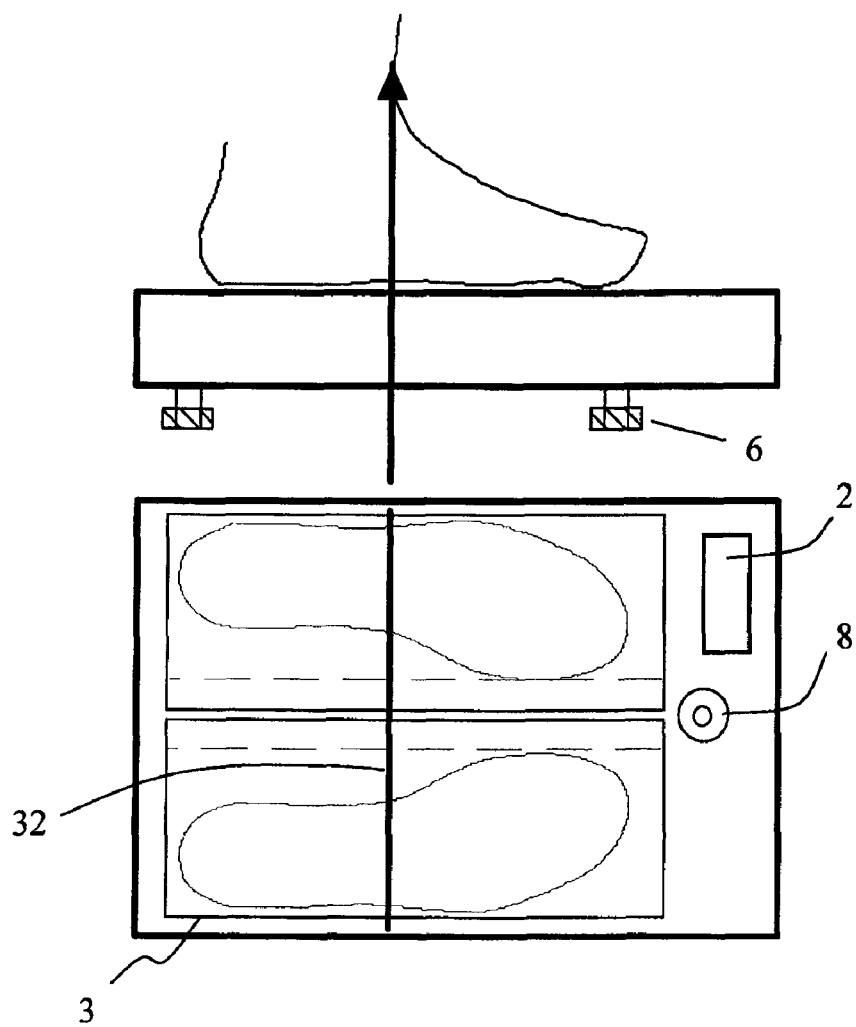
FIG. 5 is an example of how feet are positioned on a mobile plate of the apparatus of FIG. 1.

As illustrated in FIG. 5, the user has to put himself/herself in a determined position (after adjusting the horizontality of the plate (3)) relatively to the supporting plane, by following the lines or positioning grid. The feet are placed symmetrically on the plates and the front of the leg is plumb with the transverse middle line (32). In an embodiment of the invention, the display means (2) display a starting message in order to incite the user to search for the position of equilibrium. Next, the display unit may incite the user to perform a movement: crouching, punching movements, rising from the crouched position, swinging the arms, etc.

Alternatively or furthermore, a display of the weight is achieved every time the equilibrium position is reached. In one embodiment, programming may be performed in order to indicate winnings to the benefit of the user (who, for example, wins a gift or the display of a playful sequence), in the case when he/she would have managed to maintain the equilibrium position for a determined time, for example 30 or 60 seconds. Maintaining equilibrium for a long time is not obvious because four distinct elastic elements are simultaneously actuated. With the apparatus, it is possible to check that the user has his/her centre of gravity aligned with the central axis of symmetry of the plate (3). In the standing position, such an alignment is expressed by obtaining a really straight and vertical posture. The apparatus proposed according to the invention is used for correcting and controlling the verticality in different biped vertical positions, standing, half-crouching or crouching. All the advantages obtained with the apparatus described in patent EP 0 238 586-B1 of the same inventor are obtained with the scales according to the invention. It is naturally possible to use the comparison functions of the detection module (11) in order to allow viewing of the changes in equilibrium on the display means. The display may, for example, represent a bubble of a virtual bubble level, the displacement of the bubble being related to the distribution of the detected forces. The signals delivered by the sensors are then used for changing the position of a representative image of a bubble which moves around a target corresponding to the reaching of equilibrium. Reaching equilibrium may be a prerequisite for calculating or displaying the weight. Means known per se for determining the percentage of fat may be associated with the processing unit (10) and this percentage may also be displayed following the indication of the weight, for example.

The scales may also include a short distance communications interface for transmitting data to a freely mobile display device relatively to the remainder of the scales. This interface of the radiofrequency, Bluetooth®, Wifi, IR (infrared) type or other type, provides the communication with the independent display device provided with a suitable receiver.

In an alternative or complementary embodiment, tones may be emitted by an audio output connected to the processing unit (10). For example, a tone such as an "A" note may correspond to reaching equilibrium, while lower or higher tones may be broadcast in the case of disequilibrium towards one side or another.

In an embodiment of the invention, the module (11) for detecting disequilibrium has a predetermined detection threshold. Thus, when the difference between the smallest and the largest of the measured forces remains smaller than the threshold, for example, one kilogram, the detection module will not detect disequilibrium. It is understood that the detection module (11) is capable of carrying out a comparison between the representative values of the measured forces for each area with force sensor(s) (4). A detection operation may thus be performed by comparing the values obtained two by two, while thereby determining the maximum difference, and then by comparing this maximum difference with the detection threshold. A user interface (not shown) may be provided in order to allow this threshold to be parameterized. Exceeding the detection threshold means that the equilibrium of the human body is not achieved and with the display means (2), the user may be informed about this. A sound indicator may also be added for emitting sounds or audio information which depends on this distribution of the forces on the plate, therefore on proper equilibrium or not of the human body. The sound indication mode may even be substituted for the screen display indication mode. Standalone electric power supply means, such as accumulators of a known type, are provided inside the casing (30) as a power source for the display means and/or the sound indicator.

The scales (1) may be provided with a user interface including this means for selecting between notably both following operating modes:
  a conventional mode for displaying the total weight of the user of the scales, regardless of the distribution of the forces detected by each of the sensors (4); and
  a dynamic mode for displaying the total weight of the user of the scales, in which the control interface (12) prevents the display of said total weight as long as a poor distribution of the forces is detected by the detection module (11).

Thus, the user may customize the operating mode of the scales (1) via an interface of the apparatus.

One of the advantages of the apparatus according to the invention is that it resorts to the concentration of the user who should find his/her verticality, regardless of the selected vertical position: standing, half-crouching or crouching, if he/she wants to know his/her weight and/or to stop the indications relating to the disequilibrium. With the possibility of being guided by the displacements of the bubble of a level firmly attached to the plate, the user finds out on which portions of the foot he/she should exert pressure for re-centering the bubble and seeing the display of his/her weight. When it is used, the apparatus forms a really dynamic system with which the reaction forces of the deformable members (for example springs) may be set into interaction and into opposition with the various bearing forces of the subject placed on the plate (3).

When the apparatus forms scales (1), the displayed weight is the result of a small, easy, dynamic, playful, incentive and by no means dangerous exercise, an exercise during which the tactile sensitivity of all the plantar supports is activated. After his/her dynamic weighing, the user is surprised in feeling straighter, lighter, and steadier on his/her feet and more at ease during his/her displacements. He/she feels a forgotten sensation perceived in childhood, comfort of verticality and has only one desire: to move.

With the invention, a function for detecting equilibrium anomalies of the human body may advantageously be integrated into scales (1) with a plate (3) and visual and/or sound indication of weight. For this, it is sufficient for example:

to provide force sensors (4) symmetrically distributed relatively to a central axis of symmetry (S) of the plate of the scales (1);

to associate with each of the force sensors (4) a deformable member (5) in order to support along an upward direction a portion of the plate (3) and the associated sensor (4);

to connect the sensors (4) with a comparison module (11) which allows detection of the distribution of the forces; and to provide an interface (12) for controlling means for indicating weight in order to generate a modified visual and/or sound indication when a poor distribution of the forces is detected by the detection module (11), the modification thereby allowing equilibrium anomalies related to poor supports to be indicated to the user.

The user of an apparatus according to the invention feels a proper, comfortable support when he/she views his/her weight. This steadiness on the ground is thus particularly well perceived by the user who is then incited to fully exercise (concentration, involvement of his/her reflexes, while not accepting a static, passive equilibrium) in order to rapidly find his/her verticality. It should be obvious to those skilled in the art that the present invention makes embodiments possible under many other specific forms without departing from the field of application of the invention as claimed. In particular, the force sensors may be made as a FSR slab which provides the weight distribution along two axes. It is understood that it is, for example, sufficient to properly distribute the sensors according to four areas of the mobile plate (3), each of the four areas being dedicated to detecting forward or rearward pressure from one of the feet.

The invention claimed is:

1. An apparatus for detecting and correcting equilibrium anomalies of a human body, the apparatus being adapted to be used with a structure including (a) a support plate for enabling a subject to take up a position, and (b) one reference system part which is positionable on a substantially planar surface, the plate being superposed relative to the reference system part, the plate being supported by at least three deformable members each acting along a direction orthogonal to a plane defined by the reference system part, the deformable members being symmetrically distributed relative to a central axis of symmetry formed on the plate, the apparatus comprising:
   a processing unit including a processing circuit,
   a force sensor adapted to cooperate with the deformable members and for delivering a signal to the processing circuit, the processing circuit being arranged for detecting an equilibrium between the signals representing the forces and corresponding to a position of equilibrium relative to a centre of symmetry of the plate or detecting a disequilibrium between the signals representing the forces, and
   a display for displaying a piece of information in response to equilibrium being detected and for deriving a modified visual and/or sound indication in response to poor distribution of the forces being detected by the processing circuit, the modified visual and/or sound indication providing an indication of equilibrium anomalies to a user.

2. The apparatus according to claim 1, wherein the apparatus includes at least one scale and the displayed information in response to detection of equilibrium is the weight of the user.

3. The apparatus according to claim 2, comprising:
   a module for detecting disequilibrium including said processing circuit comparing data of the sensors received by the processing unit, for detecting the poor distribution of the forces detected by the sensors, and
   an interface for controlling the display for modifying the display when poor distribution of the forces is detected by the detection module.

4. The apparatus according to claim 2, including a casing having a ground supporting means, the plate being connected to the casing, each of the force sensors being located between said supporting means and the plate for deriving an electric signal representative of a force detected by the sensor, at least one processing unit for determining from the signals derived by the sensors the total weight of a subject on the scales on the plate, and display means for indicating the determined total weight, the sensors being identical and distributed in areas symmetrical to each other relative to a central axis of symmetry, one of the deformable members being associated with each of the sensor areas for supporting in an upward direction, the plate and said sensors relative to the casing.

5. The apparatus according to claim 4, comprising a leverer arrangement for horizontally adjusting the casing position.

6. The apparatus according to claim 4, wherein the ground supporting means has four legs positioned under the casing, the legs being integral with a fixed base of the reference system element.

7. The apparatus according to claim 4, wherein a bubble level is integral with the casing to indicate the horizontality of the casing.

8. The apparatus according to claim 3, wherein said control interface is arranged for displaying the total weight of the subject on the scales in response to the detection module deriving an indication of equilibrium being detected.

9. The apparatus according to claim 8, further comprising four elastic deformable members, each vertically aligned with one of the legs.

10. The apparatus according to claim 8, wherein the force sensors are distributed under four corners of the plate and the casing includes at least one vertical member connected to the reference system element, the vertical member being arranged to limit displacement of the plate supported by the deformable members.

11. The apparatus according to claim 3, wherein the module for detecting disequilibrium has a predetermined detection threshold so that the difference between the smallest and the largest of the measured forces which remains smaller than the threshold does not enable detection of disequilibrium.

12. The apparatus according to claim 3, comprising a selector for selecting between two operating modes:
   one of the modes being a conventional mode for displaying the total weight of the subject on the scales, regardless of the distribution of the forces detected by each of the sensors, and
   a second of the modes being a dynamic mode for displaying the total weight of the subject on the scales, wherein said control interface is arranged to prevent display of said total weight in response to a poor distribution of the forces detected by the detection module.

13. The apparatus according to claim 1, wherein the force sensors include sensors with variable electric resistance signal derivers.

14. The apparatus according to claim 1, wherein the plate bears elements for marking the location of two feet of the subject on the scale, each of the marking elements having at least one middle line relative to two of the force sensors.

15. The apparatus according to claim 1, comprising a short distance communications interface for transmitting data to a display device so the remainder of the apparatus is freely mobile relative to the display.

16. An apparatus for detecting and correcting equilibrium anomalies of a human body, comprising a structure including a supporting plate for enabling a subject to take up a position, and one reference system part which is positionable on a substantially planar surface, the plate being superposed relative to the reference system part, the plate being supported by at least three deformable members each acting along a direction orthogonal to a plane defined by the reference system part, the deformable members being symmetrically distributed relative to a central axis of symmetry formed on the plate, a processing unit including a processing circuit, at least one force sensor adapted to cooperate with the deformable members, each sensor being arranged for delivering a signal to the processing circuit, the processing circuit being arranged for detecting an equilibrium between the signals representing the forces and corresponding to a position of equilibrium relative to a centre of symmetry of the plate or detecting a disequilibrium between the signals representing the forces, and a display for displaying a piece of information in response to equilibrium being detected and for deriving a modified visual and/or sound indication in response to poor distribution of the forces being detected by the processing circuit, the modified visual and/or sound indication providing an indication of equilibrium anomalies to a user.

17. A method of integrating into a scale with a plate and a visual and/or sound indication of the weight of a subject on the scale, a function for detecting equilibrium anomalies of the human body, the method comprising:

symmetrically distributing force sensors relative to a central axis of symmetry formed on the plate of the scale, associating with each of the force sensors a deformable member so a portion of the plate and the associated sensor are supported in an upward direction, connecting to the sensors a detection module for detecting the distribution of the forces, and integrating an interface for controlling weight indication means so a modified visual and/or sound indication is generated in response to a poor distribution of forces being detected by the detection module, the modified visual and/or sound indication providing an indication of equilibrium anomalies to a user.

* * * * *